(12) United States Patent
Lappe et al.

(10) Patent No.: US 7,122,706 B2
(45) Date of Patent: Oct. 17, 2006

(54) PROCESS FOR PREPARING TCD-MONENAL

(75) Inventors: Peter Lappe, Dinslaken (DE); Helmut Springer, Dinslaken (DE); Rainer Lukas, Essen (DE)

(73) Assignee: Celanese Chemicals Europe GmbH, (DE)

( * ) Notice: Subject to any disclaimer, the term of this patent is extended or adjusted under 35 U.S.C. 154(b) by 44 days.

(21) Appl. No.: 10/968,760

(22) Filed: Oct. 19, 2004

(65) Prior Publication Data

US 2005/0107640 A1 May 19, 2005

(30) Foreign Application Priority Data

Nov. 8, 2003 (DE) ................. 103 52 263

(51) Int. Cl.
*C07C 45/50* (2006.01)
(52) U.S. Cl. ..................... 568/444; 568/445
(58) Field of Classification Search ............... 568/444, 568/445
See application file for complete search history.

(56) References Cited

U.S. PATENT DOCUMENTS

| 4,229,324 A | 10/1980 | Takaishi et al. |
| 4,248,802 A | 2/1981 | Kuntz |
| 5,223,648 A | 6/1993 | Herrmann et al. |
| 5,260,490 A * | 11/1993 | Forster et al. ............... 568/454 |
| 5,481,045 A | 1/1996 | Herrmann et al. |
| 6,365,782 B1 * | 4/2002 | Nakamura et al. ........... 568/444 |

FOREIGN PATENT DOCUMENTS

| DE | 36 40 615 | 6/1988 |
| DE | 197 00 804 | 8/1998 |
| EP | 0 186 075 A2 | 7/1986 |
| EP | 0 571 819 | 12/1993 |

* cited by examiner

*Primary Examiner*—Sikarl A. Witherspoon
(74) *Attorney, Agent, or Firm*—Charles A. Muserlian

(57) ABSTRACT

A process for selectively hydroformylating dicyclopentadiene to 8(9)-formyltricyclo-[5.2.1.0$^{2,6}$]dec-3-ene in a heterogeneous reaction system using an aqueous solution of transition metal compounds, containing water-soluble organic phosphorus(III) compounds in complex-bound form, of group VIII of the Periodic Table of the Elements, wherein the water-soluble organic phosphorus(III) compounds are alkali metal or alkaline earth metal salts of sulfonated arylphosphines and aryldiphosphines.

12 Claims, No Drawings

PROCESS FOR PREPARING TCD-MONENAL

The present invention relates to a process for preparing TCD-monenal {8(9)-formyltricyclo[5.2.1.0$^{2,6}$]dec-3-ene} from dicyclopentadiene (DCP).

Dicyclopentadiene (DCP), readily available by dimerizing cyclopentadiene and also prepared on the industrial scale, can be converted to compounds having important applications, to which the tricyclodecane structure imparts particular properties. The compounds, derived from DCP, having tricyclodecane structure are frequently named differently in the literature. Based on the nomenclature for DCP derivatives, disclosed by Chemiker-Zeitung, 98, 1974, pages 70 to 76, the nomenclature building on the tricyclodecane structure, also known as TCD structure, is also used hereinbelow.

Especially the hydroformylation of DCP affords TCD-aldehydes of interest, such as 8(9)-formyltricyclo[5.2.1.0$^{2,6}$]dec-3-ene, also referred to as TCD-monenal, or 3(4),8(9)-bisformyltricyclo[5.2.1.0$^{2,6}$]decane, also referred to as TCD-dialdehyde, which are further processed to give important intermediates. For instance, U.S. Pat. No. 4,229,324 discloses that TCD-monenal is condensed with further aldehydes to give products which find use in the odorants field. According to U.S. Pat. No. 4,087,467, TCD-monenal can be reduced to the saturated monoalcohol with hydrogen in the presence of platinum oxide or Raney nickel.

The preparation of aldehydes by catalytic addition of carbon monoxide and hydrogen to olefinic double bonds is known. While this reaction has previously been carried out virtually exclusively using cobalt as a catalyst, modern processes work with metallic rhodium or with rhodium compounds as catalysts which are used alone or with complex-forming ligands, for example organic phosphines or esters of phosphorous acid. There is unanimous agreement in the technical field that active catalysts under the reaction conditions are hydridocarbonyl compounds of rhodium which can be expressed by the formula $H[Rh(CO)_{4-x}L_x]$ where L denotes a ligand and x is 0 or an integer from 1 to 3.

A special case is the hydroformylation of dienes. While the hydroformylation of conjugated dienes under the customary conditions of the oxo process provides almost exclusively monoaldehydes, it is possible to obtain not only the mono- but also the disubstitution products from dicyclopentadiene (DCP) with its isolated double bonds. Owing to the risk of a retro-Diels-Alder reaction at the temperatures of the oxo process and the associated release of cyclopentadiene which is capable of complex formation with transition metals and can reduce the activity of the catalysts used, the hydroformylation has to proceed under special conditions. It has been found to be advantageous to replace the formerly customary cobalt catalyst with rhodium, which allows a high selectivity of the conversion to aldehydes to be achieved and allows the hydroformylation under conditions under which the extent of retro-Diels-Alder dissociation is lower. A review of the hydroformylation of dicyclopentadiene can be found in Chemiker-Zeitung 98, 1974, 70–76.

The prior art points out the thermal lability of TCD-aldehydes, which leads to high product losses in the course of the distillative workup of the crude hydroformylation mixture. As a consequence of this known thermal instability of the TCD-aldehydes, these aldehydes are usually not prepared in pure form, but rather further processed in their mixtures with the by-products of the oxo process (Chemikerzeitung, 98(2), 1974, page 72).

DE-B 2 918 107 describes a process for preparing TCD-monenal in which dicyclopentadiene is converted in an organic solvent with catalysis of Rh/TPP and addition of tert-amines such as triethylamine. When amines are used, contamination of the TCD-monenal with nitrogen-containing components is always to be expected.

A process for preparing TCD-monenal by hydroformylating DCP in the presence of water-soluble, sulfonated arylphosphines is disclosed by EP B1 0 186 075. In this process, also known as a heterogeneous biphasic process, catalyst systems are used which are soluble in water. Such catalysts are described, for example, in DE-C-2 627 354. In this case, the solubility of the rhodium complexes is achieved by the use of sulfonated triarylphosphines as a catalyst constituent. In this process variant, the catalyst is removed from the reaction product on completion of the hydroformylation reaction by simple phase separation of aqueous and organic phase, i.e. without distillation and thus without additional thermal process steps. EP-B1-0 186 075 points out inadequate partial conversion when Rh/TPPTS is used.

To increase the yield of the biphasic process carried out in the presence of water, EP-B1-0 186 075 proposes using ammonium salts of sulfonated arylphosphines as ligands. According to the disclosure of EP-B1-0 186 075, the use of ammonium salts increases the solubility of DCP in the aqueous, catalyst-containing phase and promotes the hydroformylation reaction.

However, the use of ammonium salts in the biphasic hydroformylation process does not always constitute the optimal solution, since ammonium salts are more expensive in comparison to the alkali metal and alkaline earth metal salts and, owing to their interface activity, their use can lead to difficulties in the phase separation between the organic aldehydic and the aqueous catalyst-containing phase. A blurred phase separation in the biphasic hydroformylation process is associated with disadvantages, since noble metal losses may result via the discharge into the organic phase and the aqueous catalyst-containing phase may be excessively contaminated with organic products, so that later workup of the spent aqueous catalyst solutions becomes complicated owing to the high proportion of organic compounds. Moreover, N-containing catalyst components in the organic phase can lead to problems in the further processing, especially in the case of use in the odorants sector.

There is therefore a need for an inexpensive and simple process for preparing TCD-monenal which overcomes the disadvantages outlined.

The invention therefore consists in a process for preparing 8(9)-formyltricyclo[5.2.1.0$^{2,6}$]dec-3-ene by hydroformylating dicyclopentadiene in a heterogeneous reaction system using an aqueous solution of transition metal compounds, containing water-soluble organic phosphorus(III) compounds in complex-bound form, of group VIII of the Periodic Table of the Elements at temperatures of from 70 to 150° C. and pressures of from 0.5 to 10 MPa with synthesis gas. In the process, the water-soluble organic phosphorus (III) compounds used are sulfonated triarylphosphines of the formula (I)

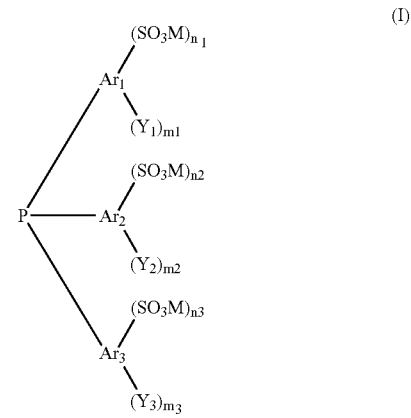

in which $Ar^1$, $Ar^2$ and $Ar^3$ are identical or different aryl groups having from 6 to 14 carbon atoms, the substituents $Y_1$, $Y_2$ and $Y_3$ are identical or different, straight-chain or branched alkyl or alkoxy radicals having from 1 to 4 carbon atoms, chlorine, bromine, hydroxyl, cyanide or nitro, or else the amino group of the formula $NR^1R^2$ in which the substituents $R^1$ and $R^2$ are the same or different and are each hydrogen, straight-chain or branched alkyl groups having from 1 to 4 carbon atoms, in which M is lithium, sodium, potassium, magnesium, calcium or barium, in which $m_1$, $m_2$ and $m_3$ are the same or different and are each integers from 0 to 5, in which $n_1$, $n_2$ and $n_3$ are the same or different and are each integers from 0 to 3, at least one of the numbers $n_1$, $n_2$ and $m_3$ being equal to or greater than 1; using, as the water-soluble organic phosphorus(III) compounds, sulfonated diphosphines of the formula II

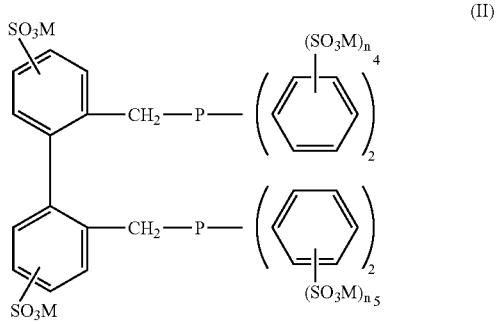

in which each $n_4$ and $n_5$ is independently 0 or 1, the compound of the formula (II) containing up to six —$SO_3M$ groups, and in which M is a monovalent metal or the equivalent of a monovalent metal; or using, as the water-soluble organic phosphorus(III) compounds, sulfonated diphosphines of the formula (III)

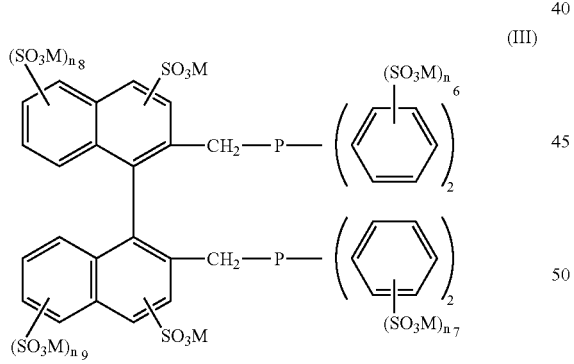

in which each $n_6$, $n_7$, $n_8$ and $n_9$ is independently 0 or 1, the compound of the formula (III) containing from four to eight —$SO_3M$ groups, and in which M is a monovalent metal or the equivalent of a polyvalent metal.

Surprisingly, and in contradiction to the teaching of EP-B1-0 186 075, it has been found that high yields can also be obtained in the preparation of TCD-monenal when, instead of ammonium salts of sulfonated arylphosphines, alkali metal or alkaline earth metal salts of sulfonated arylphosphines are used.

The reaction mixture leaving the hydroformylation reactor separates in the downstream phase separator within a short time into two clear phases, into the organic aldehydic phase and into the aqueous, catalyst-containing phase. The clear phase separation minimizes the rhodium discharge into the organic phase and the introduction of organic substances into the aqueous phase.

The TCD-monenal prepared by the process according to the invention may be further processed as a crude product without further purification steps. This is surprising inasmuch as the organic phase comprising the product of value contains homogeneously dissolved and analytically detectable amounts of phosphorus and sulfur cleavage and degradation products which are known to be catalyst poisons for many reactions.

It is likewise possible to distillatively purify the crude TCD-monenal prepared by the process according to the invention in high yields. In contrast to the opinion expressed hitherto in the prior art, that the distillation of TCD-aldehydes leads to product losses owing to the thermal lability (Chemiker-Zeitung, 98 (2), 1974, page 72), crude TCD-monenal prepared by the process according to the invention can be obtained in high purity by distillation with only very small losses.

The hydroformylation reaction of DCP is carried out as a heterogeneous reaction in a biphasic system, a reaction which is described, for example, in DE-B-26 27 354. This process is characterized by the presence of an organic phase which comprises the olefinic starting material and the reaction product, and an aqueous phase in which the catalyst is dissolved. The catalysts used are water-soluble rhodium complexes which contain water-soluble organic phorphorus (III) compounds as ligands. The water-soluble organic phosphorus(III) compounds used are sulfonated triarylphosphines of the formula (I)

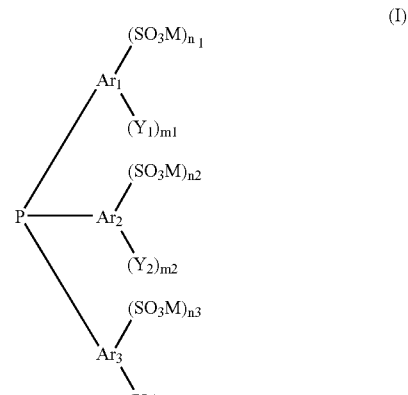

in which $Ar^1$, $Ar^2$ and $Ar^3$ are identical or different aryl groups having from 6 to 14 carbon atoms, the substituents $Y_1$, $Y_2$ and $Y_3$ are identical or different, straight-chain or branched alkyl or alkoxy radicals having from 1 to 4 carbon atoms, chlorine, bromine, hydroxyl, cyanide or nitro, or else the amino group of the formula $NR^1R^2$ in which the substituents $R^1$ and $R^2$ are the same or different and are each hydrogen, straight-chain or branched alkyl groups having from 1 to 4 carbon atoms, in which M is lithium, sodium, potassium, magnesium, calcium or barium, in which $m_1$, $m_2$ and m3 are the same or different and are each integers from 0 to 5, in which $n_1$, $n_2$ and $n_3$ are the same or different and are each integers from 0 to 3, at least one of the numbers $n_1$, $n_2$ and $n_3$ being equal to or greater than 1.

The triarylphosphines of the formula (I) preferably include those triarylphosphines in which the $Ar^1$, $Ar^2$, $Ar^3$ groups are phenyl groups; $Y_1$, $Y_2$ and $Y_3$ are the methyl group, the ethyl group, the methoxy group, ethoxy group and/or a chlorine atom; and the cationic radicals M are inorganic cations of sodium, potassium, calcium and barium. Especially suitable are those triarylphosphines in which $Ar^1$, $Ar^2$, $Ar^3$ are each a phenyl group, $m_1$, $m_2$, $m_3$ are each 0, $n_1$, $n_2$ and $n_3$ are each 0 or 1 and $n_1+n_2+n_3$ together add up to from 1 to 3, and in which the sulfonate groups are in the meta-position.

A mixture, suitable for carrying out the hydroformylation process according to the invention, of (sulfophenyl)diphenylphosphine, di(sulfophenyl)phenylphosphine and tri(sulfophenyl)phosphine) is obtained in the sulfonation of triphenylphosphine, as disclosed, for example, by DE-A 26 27 354. In the prior art, (sulfophenyl)diphenylphosphine is abbreviated to TPPMS, di(sulfophenyl)phenylphosphine to TPPDS and tri(sulfophenyl)phosphine to TPPTS.

Suitable water-soluble organic phosphorus(III) compounds are likewise sulfonated diphosphines of the formulae (II) or (II)

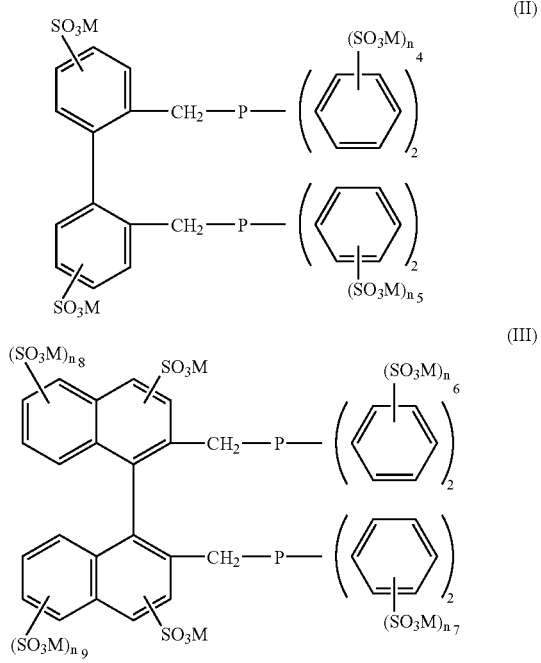

These diphosphines of the formulae (II) and (III) are disclosed by WO 98/30526.

In (II), each $n_4$ and $n_5$ is independently 0 or 1, and the compound of the formula (II) contains up to six $—SO_3M$ groups.

In (III), each $n_6$, $n_7$, $n_8$ and $n_9$ is independently 0 or 1, and the compound of the formula (III) contains from four to eight $—SO_3M$ groups.

As a consequence of the preparation by sulfonation of the corresponding diphosphines of the formulae (IIa) and (IIIa) which contain no $—SO_3M$ groups

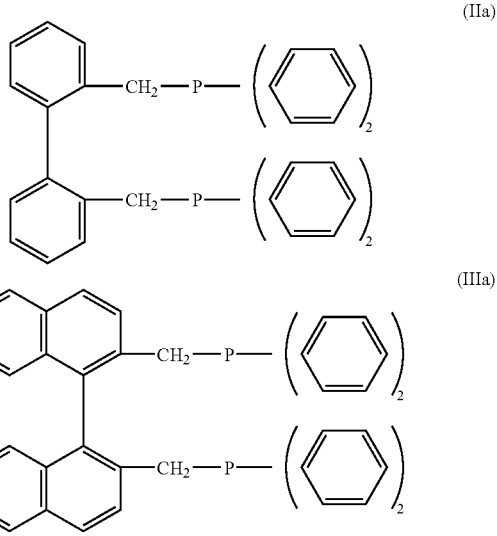

mixtures of compounds (II) and (III) with a different number of $—SO_3M$ groups are typically obtained. For instance, a compound of the formulae (II) or (III) which contains, for example, three $—SO_3M$ groups also contains compounds having only two $—SO_3M$ groups, but also compounds having four or five $—SO_3M$ groups. A compound of the formulae (II) or (III) having, for example, five $—SO_3M$ groups typically also contains compounds having only three or four $—SO_3M$ groups, but also compounds having six or seven $—SO_3M$ groups.

Compounds of the formula (II) have a maximum of six $—SO_3M$ groups, while compounds of the formula (III) have a maximum of eight $—SO_3M$ groups.

For this reason, mixtures of compounds of the formulae (II) and (III) having a different number of $—SO_3M$ groups are generally used.

In the formulae (II) and (III), M is a monovalent metal or the equivalent of a polyvalent metal, especially lithium, sodium, potassium, magnesium, calcium or barium.

It is particularly advantageous to use water-soluble complexes of rhodium, although the use of other catalytically active transition metal compounds of group VIII of the Periodic Table of the Elements is not ruled out. For instance, it is also possible to use water-soluble complexes of cobalt, iridium, nickel, palladium, platinum, iron or ruthenium, and particularly water-soluble complexes of cobalt, iridium and platinum have been found to be effective as hydroformylation catalysts.

The conditions under which the conversion proceeds may vary within wide limits and be adapted to the individual circumstances. They depend, inter alia, upon the starting material, upon the catalyst system selected and upon the desired degree of conversion. Typically, the hydroformylation of the starting materials is carried out at temperatures of from 70 to 150° C. Preference is given to maintaining temperatures of from 100 to 150° C. and especially from 110 to 140° C. The overall pressure extends over a range of from 0.5 to 10 MPa, preferably from 1 to 6 MPa and especially from 1.5 to 5 MPa. The molar ratio of hydrogen to carbon monoxide varies typically between 1:10 and 10:1; mixtures which contain hydrogen and carbon monoxide in a molar ratio of from 3:1 to 1:3, especially about 1:1, are particularly suitable.

The rhodium concentration is from 20 to 1000 ppm by weight, preferably from 50 to 800 ppm by weight and especially from 100 to 600 ppm by weight, based in each case on the aqueous catalyst solution. Although it is possible to use the rhodium-phosphorus complex having stoichiometric composition as the catalyst, it is customary to work in the presence of excess phosphorus ligand, i.e. ligand which has not entered into complexation with rhodium. Per mole of rhodium, preference is given to using from 10 to 300 mol of phosphorus in the form of a water-soluble organic phosphorus(III) compound. Particularly favorable molar ratios of rhodium to phosphorus have been found to be in the range from 1:50 to 1:150. The rhodium-phosphorus complex catalyst does not need to have a uniform composition, but rather may consist, for example, of a mixture of rhodium complexes which differ by the type of the phosphorus ligands. Equally, the free phosphorus ligand present in the aqueous catalyst solution may be composed of a mixture of different water-soluble organic phosphorus compounds.

When the catalytically active metal used is another transition metal of group VIII of the Periodic Table of the Elements, the concentration of transition metal and the molar ratio of transition metal to phosphorus vary within the ranges which are also selected in the case of rhodium. The optimal values in each case can be determined by simple routine experiments as a function of the particular transition metal used.

The catalyst is typically formed from the components of transition metal or transition metal compound, organic phosphorus compound and synthesis gas under the conditions of the hydroformylation reaction in the reaction mixture. However, it is also possible to initially preform the catalyst and subsequently feed it to the actual hydroformylation stage. The conditions of the preformation generally correspond to the hydroformylation conditions.

Dicyclopentadiene may be fed to the hydroformylation as such or in solution. Suitable solvents are water-insoluble ketones, dialkyl ethers, aliphatic nitriles, aromatic hydrocarbons such as benzene or toluene and saturated cycloaliphatic hydrocarbons such as cyclopentane or cyclohexane, or saturated aliphatic hydrocarbons.

Also with regard to the process technology and apparatus configuration of the novel process, it is possible to move within wide limits. A proven embodiment of the heterogeneous hydroformylation using an aqueous catalyst phase is described in EP-B1-0 103 810. The reaction effluent of the hydroformylation stage is separated in a phase separator into the organic product phase and into the aqueous catalyst solution. It has been found to be appropriate to circulate the catalyst solution. The crude organic product phase may then be used for subsequent reactions without further purification steps or be worked up by distillation before further processing.

To prepare the hydroformylation catalyst, the transition metal of group VIII of the Periodic Table of the Elements, especially rhodium, is used either in metallic form or as a compound. In metallic form, the transition metal is used either in the form of finely divided particles or precipitated in a thin film on a support such as activated carbon, calcium carbonate, aluminium silicate, clay earth. Suitable transition metal compounds are salts of aliphatic mono- and polycarboxylic acids, such as transition metal 2-ethylhexanoates, acetates, oxalates, propionates or malonates. In addition, salts of inorganic hydrogen and oxygen acids may be used, such as nitrates or sulfates, the different transition metal oxides or else transition metal carbonyl compounds such as $Rh_3(CO)_{12}$, $Rh_6(CO)_{16}$, $Co_2(CO)_8$, $Co_4(CO)_{16}$, $Fe(CO)_5$, $Fe_2(CO)_9$, $Ir_2(CO)_8$, $Ir_4(CO)_{12}$ or transition metal complexes, for example cyclopentadienylrhodium compounds, rhodium acetylacetonate, (1,5-cyclooctadienyl)cyclopentadienecobalt, (1,5-cyclooctadienyl)Fe(CO)$_3$, [(1,5-cyclooctadienyl)RhCl]$_2$ or (1,5-cyclooctadienyl)PtCl$_2$. Owing to the corrosive behavior of the halide ions, transition metal halide compounds are less useful.

Preference is given to using transition metal oxides and especially transition metal acetates and 2-ethylhexanoates. It has been found that rhodium oxide, rhodium acetate, rhodium 2-ethylhexanoate, cobalt oxide, cobalt acetate and cobalt 2-ethylhexanoate are particularly suitable.

The hydroformylation reaction may be carried out either batchwise or continuously.

When the reaction product of the hydroformylation reaction is distilled, operation is generally effected at a top temperature in a range from 140 to 142° C. and at a pressure in the region of 50 hPa. TCD-monenal is obtained in a purity of >99%. The distillation losses are less than 3%.

The process according to the invention permits simple and inexpensive access to TCD-monenal in high yield and in high purity. The TCD-monenal obtained by the process according to the invention can be used for different applications in an excellent manner.

The process according to the invention is illustrated in detail hereinbelow with reference to some examples, but it is not restricted to the embodiments described.

EXAMPLES

The abbreviations used in the analytical characterization of the reaction products are defined as follows:

| | |
|---|---|
| DCP | dicyclopentadiene |
| TCD-monenal | 8(9)-formyltricyclo[5.2.1.0$^{2,6}$]dec-3-ene |
| TCD-dial | 3(4),8(9)-bisformyltricyclo[5.2.1.0$^{2,6}$]decane |
| Tri-CP | tricyclopentadiene |
| TPPTS means | sodium triphenylphosphinetrisulfonate |

Preparation of TCD-dialdehyde

Example 1

A 5 l autoclave is initially charged with 2119 g of TPPTS solution having a P(III) content of 472 mmol/kg which are admixed with 160.2 g of Rh solution (Rh content: 6,423 mg/kg). Afterward, a mixture of 661.1 g of dicyclopentadiene (technical grade, DCP content: 93.72% by weight) and 283.0 g of toluene is added. The reaction mixture is heated to 135° C. and converted at a synthesis gas pressure of 2.5 MPa and a reaction time of 6 hours.

After the end of the reaction, the mixture is cooled and the upper, organic phase is removed from the aqueous catalyst phase by phase separation. The remaining catalyst phase is again admixed with a mixture of dicyclopentadiene and toluene and again converted. This procedure is repeated a total of eight times.

The organic phases are weighed and analyzed by gas chromatography.

GC Analysis (in Area %):

|  | 1st batch | 3rd batch | 5th batch | 7th batch | 9th batch |
|---|---|---|---|---|---|
| First runnings components | 0.32 | 0.31 | 0.34 | 0.37 | 0.37 |
| Toluene | 39.22 | 27.03 | 29.45 | 29.47 | 29.96 |
| DCP | 3.66 | 4.13 | 4.55 | 4.60 | 5.24 |
| TCD-monenal | 52.85 | 63.80 | 61.20 | 61.16 | 59.94 |
| TCD-dial | 0.56 | 0.95 | 0.80 | 0.83 | 0.82 |
| Tri-CP | 0.39 | 0.45 | 0.46 | 0.41 | 0.42 |
| Others | 3.00 | 3.33 | 3.20 | 3.16 | 3.25 |
| Org. phase (g) | 1,158 | 1,091 | 1,073 | 1,070 | 1,086 |
| TCD-monenal yield (%) |  | 92.9 | 90.1 | 89.7 | 90.4 |

The increased toluene value in the 1st batch results from the toluene present in the Rh solution and is discharged with the organic product of value phase after the first batch and is not taken into account in the consideration of the yields. The thick oil contents (determined by a flash distillation on a Claisen head with condenser) in all experiments are less than 2% by weight.

The yields of TCD-monenal in this experimental series (experiments 3–9) are 90–93%; the average value is 90.8%.

Example 2

The Rh/TPPTS catalyst solution remaining from example 1 is admixed according to the procedure of example 1 with 661.1 g of dicyclopentadiene (technical grade, DCP content: 93.72% by weight) and converted under the same reaction conditions (135° C., 2.5 MPa, 6 hours).

The organic phases are weighed and analyzed by gas chromatography.

GC Analysis (in Area %):

|  | 10th batch | 11th batch | 13th batch | 15th batch |
|---|---|---|---|---|
| First runnings components | 0.26 | 0.32 | 0.33 | 0.35 |
| Toluene | 0.74 | 0.12 | 0.01 | <0.01 |
| DCP | 1.37 | 2.71 | 2.84 | 3.47 |
| TCD-monenal | 90.18 | 89.37 | 89.34 | 88.85 |
| TCD-dial | 1.74 | 1.66 | 1.49 | 1.49 |
| Tri-CP | 0.50 | 0.53 | 0.62 | 0.55 |
| Others | 5.21 | 5.29 | 5.37 | 5.28 |
| Org. phase (g) | 786 | 807 | 802 | 808 |
| TCD-monenal yield (%) | 94.0 | 95.0 | 94.2 | 94.4 |

The thick oil contents (determined by a flash distillation on a Claisen head with condenser) in all experiments are below 2% by weight.

The yields of TCD-monenal in this experimental series (experiments 10–15) are 94–95%; the average value is 94.4%.

Example 3

Pure TCD-monenal is obtained by distillation on a column having 4.5 theoretical plates; for this purpose, the following typical hydroformylation products (800.9 g) is used:

GC Analysis (in Area %):

| First runnings components | 0.61 |
|---|---|
| Toluene | 29.81 |
| DCP | 3.29 |
| TCD-monenal | 62.06 |
| TCD-dial | 0.67 |
| Tri-CP | 0.29 |
| Others | 3.27 |

After removal of first runnings components, solvent (toluene) and intermediate runnings components (302.5 g in total) at a reflux ratio (RR) of 2:1 or 5:1, a max. top temperature of 140° C. and a pressure of 50 hPa, a pure fraction (482.9 g) is isolated in a boiling range of 141–142° C. (top temperature) at 50 hPa and a RR of 0.5:1 with the following composition.

GC Analysis (in Area %):

| Toluene | 0.02 |
|---|---|
| DCP | 0.03 |
| TCD-monenal | 99.02 |
| TCD-dial | 0.04 |
| Tri-CP | 0.20 |
| Others | 0.69 |

This corresponds to a distillative yield of 96.2%. The amount of residue is 15.5 g (1.9% of batch).

As shown by example 3, TCD-monenal can be purified distillatively with an outstanding yield.

Example 4

According to example 1, 2,119 g of TPPTS solution (P(III) content: 472 mmol/kg) and 160.2 g of rhodium 2-ethylhexanoate solution (Rh content: 6,423 mg/kg) are initially charged. To this solution are added 661.1 g of dicyclopentadiene (DCP content: 93.72%) and 283 g of toluene which are reacted at temperatures of 120–135° C. and a reaction time of 6 hours.

The organic phases are weighed and analyzed by GC.

GC Analysis (in Area %):

|  | Temperature (° C.) | | | |
|---|---|---|---|---|
|  | 135 | 130 | 125 | 120 |
| First runnings components | 0.67 | 0.65 | 0.61 | 0.56 |
| Toluene | 32.80 | 32.20 | 31.10 | 31.50 |
| DCP | 3.99 | 8.09 | 14.01 | 21.23 |
| TCD-monenal | 58.71 | 56.03 | 51.91 | 44.52 |
| TCD-dial | 0.94 | 0.75 | 0.49 | 0.44 |
| Tri-CP | 0.55 | 0.40 | 0.36 | 0.31 |
| Others | 2.34 | 1.88 | 1.52 | 1.44 |
| Org. phase (g) | 1,072 | 1,068 | 1,058 | 1,062 |
| Selectivity (%) | 96.4 | 96.8 | 96.4 | 96.5 |

Example 5

According to example 1, 2119 g of TPPTS solution (P(III) content: 472 mmol/kg) and 160.2 g of rhodium 2-ethylhexanoate solution (Rh content: 6,423 mg/kg) are initially charged. To this solution are added 661.1 g of dicyclopentadiene (DCP content: 93.72%) and 283 g of toluene which are reacted at a temperature of 125° C. and a pressure of 2.5 MPa. Samples are taken over a period of 6–15 hours and analyzed by gas chromatography.

GC Analysis (in Area %):

|  | Reaction time (hours) | | | | |
|---|---|---|---|---|---|
|  | 6 | 8 | 10 | 12 | 15 |
| First runnings components | 0.61 | 0.58 | 0.62 | 0.56 | 0.55 |
| Toluene | 31.10 | 29.60 | 30.15 | 29.60 | 29.25 |
| DCP | 14.01 | 9.62 | 5.82 | 3.50 | 1.73 |
| TCD-monenal | 51.91 | 57.45 | 60.62 | 63.12 | 64.92 |
| TCD-dial | 0.49 | 0.53 | 0.61 | 0.83 | 1.09 |
| Tri-CP | 0.36 | 0.40 | 0.40 | 0.42 | 0.39 |
| Others | 1.52 | 1.82 | 1.78 | 1.97 | 2.07 |

Example 6

According to example 1, 2,119 g of TPPTS solution (P(III) content: 472 mmol/kg) and 160.2 g of rhodium 2-ethylhexanoate solution (Rh content: 6,423 mg/kg) are initially charged. To this solution are added 661.1 g of dicyclopentadiene (DCP content: 93.72%) and 283 g of toluene which are reacted at a temperature of 130° C. and a pressure of 2.5 MPa. Samples are taken over a period of 4–10 hours and analyzed by gas chromatography.

GC Analysis (in Area %):

|  | Reaction time (hours) | | | |
|---|---|---|---|---|
|  | 4 | 6 | 8 | 10 |
| First runnings components | 0.80 | 0.65 | 0.75 | 0.62 |
| Toluene | 30.40 | 31.20 | 30.50 | 30.70 |
| DCP | 16.36 | 8.09 | 4.31 | 2.36 |
| TCD-monenal | 49.76 | 57.03 | 60.99 | 62.89 |
| TCD-dial | 0.59 | 0.75 | 0.94 | 1.00 |
| Tri-CP | 0.28 | 0.40 | 0.38 | 0.42 |
| Others | 1.81 | 1.88 | 2.13 | 2.01 |

Example 7

According to example 1, 874 g of TPPTS solution (P(III) content: 472 mmol/kg), 66.0 g of rhodium 2-ethylhexanoate solution (Rh content: 6,423 mg/kg) and 1,245 g of water are initially charged. To this solution are added 661.1 g of dicyclopentadiene (DCP content: 93.72%) and 283 g of toluene which are reacted at a temperature of 125° C. and a pressure of 2.5 MPa. Samples are taken over a period of 6–16 hours and analyzed by gas chromatography.

GC Analysis (in Area %):

|  | Reaction time (hours) | | | | |
|---|---|---|---|---|---|
|  | 6 | 8 | 10 | 12 | 14 |
| First runnings components | 0.42 | 0.35 | 0.21 | 0.07 | 0.14 |
| Toluene | 30.61 | 29.95 | 29.76 | 30.05 | 29.40 |
| DCP | 14.50 | 8.34 | 4.85 | 2.87 | 1.34 |
| TCD-monenal | 52.26 | 58.84 | 62.43 | 64.07 | 65.87 |
| TCD-dial | 0.42 | 0.56 | 0.70 | 0.77 | 0.99 |
| Tri-CP | 0.28 | 0.28 | 0.28 | 0.35 | 0.28 |
| Others | 1.51 | 1.68 | 1.76 | 1.82 | 1.98 |

Example 8

According to example 1, 874.0 g of TPPTS solution (P(III) content: 472 mmol/kg), 64.3 g of rhodium 2-ethylhexanoate solution (Rh content: 6,603 mg/kg) and 1,245 g of water are initially charged. To this solution are added 661.1 g of dicyclopentadiene (DCP content: 93.72%) and 283 g of toluene which are reacted at a temperature of 125° C. and a pressure of 2.5 MPa. Samples are taken over a period of 8–15 hours and analyzed by gas chromatography.

GC Analysis (in Area %):

|  | Reaction time (hours) | |
|---|---|---|
|  | 8 | 15 |
| First runnings components | 0.92 | 0.63 |
| Toluene | 29.55 | 29.83 |
| DCP | 8.38 | 1.89 |
| TCD-monenal | 58.90 | 63.80 |
| TCD-dial | 0.49 | 0.42 |
| Tri-CP | 0.49 | 1.12 |
| Others | 1.27 | 2.31 |

Example 9

According to example 1, 654.0 g of TPPTS solution (P(III) content: 472 mmol/kg), 48.1 g of rhodium 2-ethylhexanoate solution (Rh content: 6,603 mg/kg) and 1,465.0 g of water are initially charged. To this solution are added 661.1 g of dicyclopentadiene (DCP content: 93.72%) and 283 g of toluene which are reacted at a temperature of 125° C. and a pressure of 2.5 MPa. After a reaction time of 8 hours, the reaction mixture is analyzed by gas chromatography.

GC analysis (in Area %):

| First runnings components | 0.56 |
|---|---|
| Toluene | 30.30 |
| DCP | 1.53 |
| TCD-monenal | 64.19 |
| TCD-dial | 1.05 |
| Tri-CP | 0.35 |
| Others | 2.02 |

Example 10

According to example 1, 436.0 g of TPPTS solution (P(III) content: 472 mmol/kg), 32.1 g of rhodium 2-ethylhexanoate solution (Rh content: 6,603 mg/kg) and 1,683.0 g of water are initially charged. To this solution are added 661.1 g of dicyclopentadiene (DCP content: 93.72%) and 283 g of toluene which are reacted at a temperature of 125° C. and a pressure of 2.5 MPa. After a reaction time of 16 hours, the reaction mixture is analyzed by gas chromatography.

GC Analysis (in Area %):

| First runnings components | 0.78 |
|---|---|
| Toluene | 29.50 |
| DCP | 3.45 |
| TCD-monenal | 62.60 |
| TCD-dial | 0.85 |
| Tri-CP | 0.56 |
| Others | 2.26 |

As the examples show, dicyclopentadiene can be convertedselectively to TCD-monenal in high yields in the presence of an aqueous sodium-TPPTS 10 solution. In the phase separation between the organic product of value phase and the aqueous catalyst phase, no phase separation problems occur. In the distillative purification of the crude product, residues occur in only a very small amount.

What is claimed is:

1. A process for preparing 8(9)-formyltricyclo[5.2.1.0$^{2,6}$]dec-3-ene by hydroformylating dicyclopentadiene in a heterogeneous reaction system using an aqueous solution of transition metal compounds, containing water-soluble organic phosphorus(III) compounds in complex-bound form, of group VIII of the Periodic Table of the Elements at temperatures of from 70 to 150° C. and pressures of from 0.5 to 10 MPa with synthesis gas, which comprises using, as the water-soluble organic phosphorus(III) compounds selected from the group consisting of A) sulfonated triarylphosphines

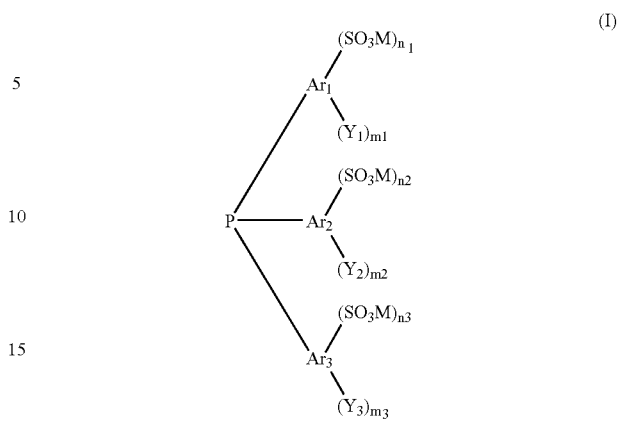

in which $Ar^1$, $Ar^2$ and $Ar^3$ are individually aryl of 6 to 14 carbon atoms, $Y_1$, $Y_2$ and $Y_3$ are individually selected from the group consisting of alkyl or alkoxy of 1 to 4 carbon atoms, chlorine, bromine, hydroxyl, cyanide, nitro and —$NR^1R^2$ in which $R^1$ and $R^2$ are consisting of lithium, sodium, potassium, magnesium, calcium and barium, $m_1$, $m_2$ and $m_3$ are individually integers from 0 to 5, $n_1$, $n_2$ and $n_3$ are individually integers from 0 to 3, at least one $n_1$, $n_2$ and $n_3$ being equal to or greater than 1;

B) sulfonated diphosphines of the formula

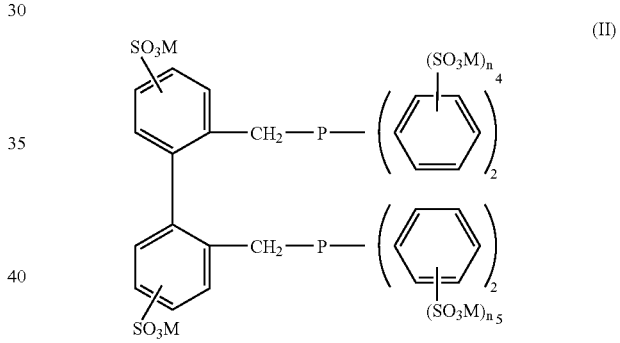

in which $n_4$ and $n_5$ are individually 0 or 1, the compound of formula (II) containing up to six —$SO_3M$ groups, and M is a monovalent metal or the equivalent of a monovalent metal; and C) sulfonated diphosphines of the formula

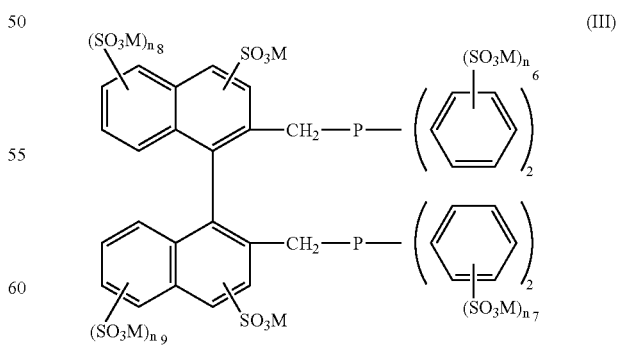

in which $n_6$, $n_7$, $n_8$ and $n_9$ are individually 0 to 1, the compound of formula (III) containing from four to eight —$SO_3M$, and M is a monovalent metal or the equivilant of a polyvalent metal.

2. The process of claim 1, wherein the resulting 8(9)-formyltricyclo[5.2.1.0$^{2,6}$]dec-3-ene is distilled.

3. The process of claim 1, wherein $Ar^1$, $Ar^2$, $Ar^3$ are phenyl, $m_1$, $m_2$, and $m_3$ are 0, $n_1$, $n_2$, $n_3$ are individually 0 or 1 and $n_1+n_2+n_3$ together add up to 1 to 3, and the sulfonate groups are in the meta-position.

4. The process of claim 1, wherein the transition metal compounds of group VIII of the Periodic Table of the Elements used are compounds of a metal selected from the group consisting of rhodium, cobalt, iridium, nickel, palladium, platinum, iron or ruthenium.

5. The process of claim 1, wherein the transition metal compounds of group VIII of the Periodic Table of the Elements used are compounds of rhodium.

6. The process of claim 1, wherein the reaction temperature is from 100 to 150° C. and the pressure is from 1 to 6 MPa.

7. The process of claim 1, wherein the rhodium concentration is from 20 to 1000 ppm by weight, based in each case on the aqueous catalyst solution.

8. The process of claim 1, wherein from 10 to 300 mol of phosphorous in the form of the water-soluble organic phosphorous compound are used per mole of rhodium.

9. The process of claim 6 wherein the reaction temperature is 110 to 140° C. and the pressure is 1.5 to 5 Mpa.

10. The process of claim 7 wherein the rhodium concentration is 50 to 800 ppm by weight.

11. The process of claim 7 wherein the rhodium concentration is 100 to 600 ppm by weight.

12. The process of claim 8 wherein the amount of phosphorous is 50 to 150 mol.

* * * * *